United States Patent
Hara et al.

(10) Patent No.: US 7,160,625 B2
(45) Date of Patent: Jan. 9, 2007

(54) INSULATING FILM MATERIAL CONTAINING AN ORGANIC SILANE COMPOUND, ITS PRODUCTION METHOD AND SEMICONDUCTOR DEVICE

(75) Inventors: Daiji Hara, Yamaguchi-ken (JP); Keisuke Yoshida, Yamaguchi-ken (JP)

(73) Assignee: Tosoh Corporation, Yamaguchi-ken (JP)

( * ) Notice: Subject to any disclaimer, the term of this patent is extended or adjusted under 35 U.S.C. 154(b) by 253 days.

(21) Appl. No.: 10/354,052

(22) Filed: Jan. 30, 2003

(65) Prior Publication Data

US 2003/0180550 A1 Sep. 25, 2003

(30) Foreign Application Priority Data

| | | | |
|---|---|---|---|
| Jan. 31, 2002 | (JP) | | 2002-023988 |
| Apr. 15, 2002 | (JP) | | 2002-112130 |
| Nov. 15, 2002 | (JP) | | 2002-332100 |
| Nov. 28, 2002 | (JP) | | 2002-346225 |
| Nov. 28, 2002 | (JP) | | 2002-346226 |

(51) Int. Cl.
*B32B 9/04* (2006.01)

(52) U.S. Cl. .................. 428/447; 427/249.15; 556/482
(58) Field of Classification Search ................ 428/447; 427/249.15; 556/482
See application file for complete search history.

(56) References Cited

U.S. PATENT DOCUMENTS

| | | | | |
|---|---|---|---|---|
| 4,711,820 A | * | 12/1987 | Arkles et al. ................ 428/429 |
| 5,061,514 A | * | 10/1991 | Boeglin ....................... 427/578 |
| 6,303,047 B1 | * | 10/2001 | Aronowitz et al. ............ 252/1 |
| 6,583,048 B1 | * | 6/2003 | Vincent et al. ............. 438/623 |

FOREIGN PATENT DOCUMENTS

| | | |
|---|---|---|
| EP | 0 826 791 A2 | 3/1998 |
| JP | 2000-302791 | 10/2000 |

* cited by examiner

*Primary Examiner*—Margaret G. Moore
(74) *Attorney, Agent, or Firm*—Sughrue Mion, PLLC

(57) ABSTRACT

An insulating film material formed by chemical vapor deposition, which contains an organic silane compound having such a structure that at least one secondary hydrocarbon group and/or tertiary hydrocarbon group is directly bonded to a silicon atom.

4 Claims, 1 Drawing Sheet

INSULATING FILM MATERIAL CONTAINING AN ORGANIC SILANE COMPOUND, ITS PRODUCTION METHOD AND SEMICONDUCTOR DEVICE

BACKGROUND OF THE INVENTION

1. Field of the Invention

The present invention relates to a low-dielectric constant interlayer insulating film material used in multilevel interconnection technology in logic ULSI. Particularly, it relates to an insulating film material containing a silane compound for plasma polymerization, its production method and its use.

2. Discussion of Background

In the production technology in the field of integrated circuit in an electronics industry, demand for high integration and high speed has been increasing. With respect to silicon ULSI, particularly logic ULSI, performance of the wiring which connects MOSFET, rather than the performance of MOSFET itself by its miniaturization has been problematic. Namely, in order to overcome the problem of wiring delay due to multilevel interconnection, reduction of wiring resistance and reduction of capacity between wirings and between layers have been required.

Accordingly, at present, introduction of copper wiring having a low electric resistance and having a migration resistance, instead of aluminum wiring used for the most part of the integrated circuit, is essential, and a process comprising seed formation by sputtering or chemical vapor deposition (hereinafter referred to simply as CVD) method, followed by copper plating, has been used practically.

As the low-dielectric constant interlayer insulating film material, various ones have been proposed. Heretofore, as the inorganic system, silicon dioxide ($SiO_2$), silicon nitride and phosphosilicate glass, and as the organic system, polyimides have been employed. In recent years, with a purpose of obtaining a more homogeneous interlayer insulating film, it has been proposed that a tetraethoxysilane monomer is preliminarily hydrolyzed, i.e., subjected to polycondensation to obtain $SiO_2$, which is used as a coating material called "spin on glass" (inorganic SOG), and it has been proposed to use a polysiloxane obtained by polycondensation of an organic alkoxysilane monomer as organic SOG.

Further, as a method of forming the insulating film, there are two methods including a coating method comprising coating an insulating film polymer solution by e.g. spin coating to carry out film formation and a CVD method comprising plasma polymerization mainly in a plasma CVD apparatus to carry out film formation.

With respect to the characteristics of the film formation method, in the plasma CVD method, adhesion properties to a barrier metal and a copper wiring material which is a wiring material are good, on the contrary, uniformity of the film may be problematic in some cases. In the coating method, although the uniformity of the film may be good, three steps of coating, solvent removal and heat treatment are required, such being economically disadvantageous as compared with the CVD material, and further, adhesion properties to a barrier metal and a copper wiring material which is a wiring material, and uniform coating itself of the coating liquid on a miniaturized substrate structure tend to be problematic in many cases.

With respect to the materials in the coating method, a method of making materials be porous has been proposed so as to achieve an ultra low-k material having a dielectric constant of at most 2.5, more preferably at most 2.0. A method of dispersing organic component fine particles which easily decomposed into an organic or inorganic material matrix, followed by heat treatment to make the material be porous, and a method of depositing $SiO_2$ ultrafine particles formed by evaporation of silicon and oxygen in a gas, to form a thin film of $SiO_2$ ultrafine particles, may, for example, be mentioned.

However, although these methods of making the material be porous, are effective to achieve a low dielectric constant, mechanical strength tends to decrease, whereby chemical mechanical polishing (CMP) may be difficult, or increase of the dielectric constant and wiring corrosion due to absorption of moisture may be caused in some cases.

Accordingly, the market further requires a well-balanced material which satisfies all the requirements such as a low dielectric constant, an adequate mechanical strength, adhesion properties to a barrier metal, prevention of copper dispersion, plasma ashing resistance and moisture absorption resistance. In order to satisfy these requirements to a certain extent, an organic silane type material having an increased proportion of carbon in the organic substituent based on silane, thereby having characteristics intermediate between the organic polymer and the inorganic polymer has been proposed.

For example, JP-A-2000-302791 proposes a method to obtain an interlayer insulating film not being porous and having a dielectric constant of at most 2.4, by using a coating solution obtained by hydrolysis and polycondensation of a silicon compound having an adamantyl group by a sol-gel method in the presence of an aqueous acid solution. However, this material is a material for the coating method, and there are still problems of the above-described film formation method by the film coating method.

Further, JP-A-2002-110670 discloses that a methylsilane oxide film is obtained by using trimethylsilane, dimethyldimethoxysilane, diethyldiethoxysilane or the like and an oxidizing agent such as oxygen, dinitrogen oxide or carbon dioxide as materials by means of a PECVD apparatus. However, as shown in Examples as described hereinafter, with a silane having only a primary short chain alkyl group, there are such problems that the PECVD film formation rate may be inadequate, or the carbon uptake amount, which has a role to achieve a low dielectric constant, tends to be small.

SUMMARY OF THE INVENTION

Under these circumstances, the present invention has been made to overcome the above problems, and it is an object of the present invention to provide a novel low-dielectric material, particularly a material for a low-dielectric constant insulating film, containing an alkylsilane compound suitable for a PECVD apparatus, and to provide an insulating film employing it and a semiconductor device containing such an insulating film.

The present inventors have found that an organic silane compound having such a structure that at least one secondary hydrocarbon group and/or tertiary hydrocarbon group is directly bonded to a silicon atom, is suitable as a material for an insulating film, particularly a low-dielectric constant interlayer insulating film for a semiconductor device, and the present invention has been accomplished on the basis of this discovery.

Namely, the present invention is to provide an insulating film material formed by chemical vapor deposition, which contains an organic silane compound of the following formula (1):

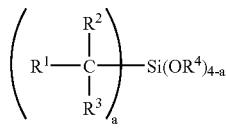

wherein each of $R^1$, $R^2$ and $R^3$ is a $C_{1-20}$ hydrocarbon group, provided that $R^1$, $R^2$ and $R^3$ may be bonded to each other to form a cyclic structure, $R^4$ is a $C_{1-10}$ hydrocarbon group or a hydrogen atom, and a is an integer of from 1 to 3, an organic silane compound of the following formula (2):

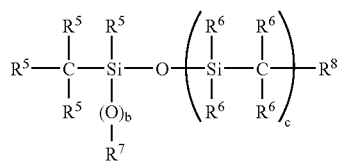

wherein each of $R^5$ and $R^6$ is a $C_{1-20}$ hydrocarbon group, each of $R^7$ and $R^8$ is a hydrogen atom or a $C_{1-20}$ hydrocarbon group, provided that a plurality of $R^5$'s, or $R^6$ and $R^8$ may be bonded to each other to form a cyclic structure, and each of b and c is 0 or 1, or an organic silane compound of the following formula (3):

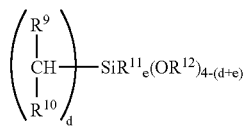

wherein each of $R^9$, $R^{10}$ and $R^{11}$ is a $C_{1-20}$ hydrocarbon group, provided that $R^9$ and $R^{10}$ may be bonded to each other to form a cyclic structure, $R^{12}$ is a $C_{1-10}$ hydrocarbon group or a hydrogen atom, d is an integer of from 1 to 3, e is an integer of from 0 to 2, and d+e is an integer of at most 3.

DETAILED DESCRIPTION OF THE PREFERRED EMBODIMENTS

Figure 1:
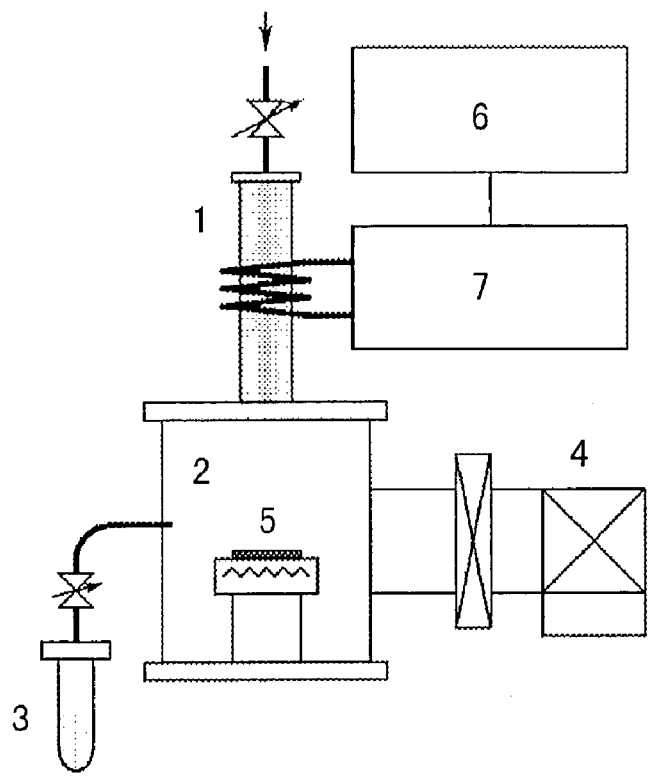
FIG. 1 is a schematic view illustrating the constitution of a PECVD apparatus.

In the above formula (1), each of $R^1$, $R^2$ and $R^3$ is a $C_{1-20}$ saturated or unsaturated hydrocarbon group, and may have any of linear, branched chain and cyclic structures. Further, a combination thereof is included in the present invention. If the carbon number exceeds 20, it tends to be difficult to obtain a material such as a corresponding organic halide, or even if it can be obtained, the purity tends to be low in some cases.

Taking stable use in a PECVD apparatus into consideration, a $C_{1-10}$ hydrocarbon group is particularly preferred from such a viewpoint that the vapor pressure of the organic silane compound will not be too low.

Examples of the hydrocarbon group for each of $R^1$, $R^2$ and $R^3$ are not particularly limited, and a $C_{1-20}$, preferably $C_{1-10}$, alkyl group, an aryl group, an arylalkyl group and an alkylaryl group may be mentioned. $R^1$, $R^2$ and $R^3$ may be the same or different.

As examples of a case where $R^1$, $R^2$ and $R^3$ are not bonded to each other, methyl, ethyl, n-propyl, i-propyl, n-butyl, i-butyl, sec-butyl, tert-butyl, n-pentyl, tert-amyl, n-hexyl, cyclohexyl, phenyl and toluyl group may, for example, be mentioned.

As examples of a case where $R^1$, $R^2$ and $R^3$ are bonded to each other, a 1-adamantyl group may be mentioned as a representative example. Particularly preferred as a tertiary hydrocarbon group from an economical viewpoint is tert-butyl wherein each of $R^1$, $R^2$ and $R^3$ is methyl, tert-amyl wherein each of $R^1$ and $R^2$ is methyl and $R^3$ is ethyl, and 1-adamantyl wherein $R^1$, $R^2$ and $R^3$ are bonded to one another.

$R^4$ is a $C_{1-10}$ hydrocarbon group or a hydrogen atom, the hydrocarbon group is a saturated or unsaturated hydrocarbon group and may have any of linear, branched chain and cyclic structures. If the carbon number exceeds 10, the vapor pressure of the formed organic silane tends to be low and its use in a PECVD apparatus tends to be difficult in some cases, such being unfavorable.

$R^4$ is preferably methyl, ethyl, n-propyl, i-propyl, n-butyl, i-butyl, sec-butyl or tert-butyl which is a $C_{1-4}$ hydrocarbon group, in view of preparation of the material.

a is an integer of from 1 to 3. Namely, the organic silane compound of the formula (1) is a trialkoxysilane substituted with a hydrocarbon group wherein a=1, a dialkoxysilane disubstituted with hydrocarbon groups wherein a=2 or an alkoxysilane trisubstituted with hydrocarbon groups wherein a=3. A mixture thereof is included in the present invention.

Specific examples of the organic silane compound of the formula (1) include tert-butyltrimethoxysilane, di-tert-butyldimethoxysilane, tert-amyltrimethoxysilane, di-tert-amyldimethoxysilane, 1-adamantyltrimethoxysilane, di(1-adamantyl)dimethoxysilane, tert-butyltriethoxysilane, di-tert-butyldiethoxysilane, tert-amyltriethoxysilane, di-tert-amyldiethoxysilane, 1-adamantyltriethoxysilane, di(1-adamantyl)diethoxysilane, tert-butyl-tri-i--propoxysilane, di-tert-butyldi-i-propoxysilane, tert-amyl-tri-i-propoxysilane, di-tert-amyl-di-1-propoxysilane, 1-adamantyl-tri-i-propoxysilane, di(1-adamantyl)di-i-propoxysilane, 1-twistyl trimethoxysilane, di(1-twistyl)dimethoxysilane, 1-diamantyltrimethoxysilane, di(1-diamantyl)dimethoxysilane, 1-triptycyltrimethoxysilane and di(1-triptycyl)dimethoxysilane.

In the above formula (2), each of $R^5$ and $R^6$ is a $C_{1-20}$ saturated or unsaturated hydrocarbon group, and may have any of linear, branched chain and cyclic structures. Further, a combination thereof is included in the present invention. If the carbon number exceeds 20, it tends to be difficult to obtain a material such as a corresponding organic halide, or even if it can be obtained, the purity tends to be low in some cases.

Taking stable use in a CVD apparatus into consideration, particularly preferred is a $C_{1-10}$ hydrocarbon group. If the carbon number exceeds 10, the vapor pressure of the formed organic silane tends to be low, and its use in a PECVD apparatus tends to be difficult in some cases, such being unfavorable.

Examples of the hydrocarbon group for each of $R^5$ and $R^6$ are not particularly limited, and a $C_{1-20}$, preferably $C_{1-10}$ alkyl group, an aryl group, an arylalkyl group and an alkylaryl group may be mentioned. $R^5$ and $R^6$ may be the same or different.

As examples of a case where a plurality of $R^5$'s are not bonded to each other, methyl, ethyl, n-propyl, i-propyl, n-butyl, i-butyl, sec-butyl, tert-butyl, n-pentyl, tert-amyl, n-hexyl, cyclohexyl, phenyl and toluyl may, for example, be mentioned.

As an example of a case where a plurality of $R^5$'s are bonded to each other, 1-adamantyl may be mentioned as a representative example.

Each of $R^7$ and $R^8$ is a hydrogen atom or the same hydrocarbon group as defined for each of $R^5$ and $R^6$. $R^6$ and $R^8$ may be bonded to each other to form a cyclic structure, and the same example as in the above case where a plurality of $R^5$'s are bonded to each other may be mentioned.

Each of b and c is 0 or 1. Namely, when b=1 and c=0, the organic silane compound of the formula (2) is a dialkoxysilane disubstituted with hydrocarbon groups, when b=0 and c=0, the compound of the formula (2) is an alkoxysilane trisubstituted with hydrocarbon groups, and when b=0 and c=1, the compound of the formula (2) is a disiloxane hexa-substituted with hydrocarbon groups. A mixture thereof is included in the present invention.

Specific examples of the organic silane compound of the formula (2) include:

(A) Tert-butylmethyldiethoxysilane, tert-butylmethyldimethoxysilane, tert-butylmethyldihydroxysilane, tert-butylethyldiethoxysilane, tert-butylethyldimethoxysilane, tert-butylethyldihydroxysilane, tert-butylphenyldiethoxysilane, tert-butylphenyldimethoxysilane, tert-butylphenyldihydroxysilane and the like, (B) 1-Adamantylmethyldiethoxysilane, 1-adamantylmethyldimethoxysilane, 1-adamantylmethyldihydroxysilane, 1-adamantylethyldiethoxysilane, 1-adamantylethyldimethoxysilane, 1-adamantylethyldihydroxysilane, 1-adamantylphenyldiethoxysilane, 1-adamantylphenyldimethoxysilane, 1-adamantylphenyldihydroxysilane and the like, (C) Tert-butyldimethylhydroxysilane, tert-butyldimethylmethoxysilane, tert-butyldimethylethoxysilane, tert-butyldiethylhydroxysilane, tert-butyldiethylmethoxysilane, tert-butyldiethylethoxysilane, tert-butyldiphenylhydroxysilane, tert-butyldiphenylmethoxysilane, tert-butyldiphenylethoxysilane and the like, (D) 1-Adamantyldimethyl hydroxysilane, 1-adamantyldimethylmethoxysilane, 1-adamantyldimethylethoxysilane, 1-adamantyldiethylhydroxysilane, 1-adamantyldiethylmethoxysilane, 1-adamantyldiethylethoxysilane, 1-adamantyldiphenylhydroxysilane, 1-adamantyldiphenylmethoxysilane, 1-adamantyldiphenylethoxysilane and the like, (E) 1,3-Di-tert-butyl-1,1,3,3-tetramethyldisiloxane, 1,3-di-tert-butyl-1,1,3,3-tetraethyldisiloxane, 1,3-di-tert-butyl-1,1,3,3-tetraphenyldisiloxane and the like, and (F) 1,3-Di(1-adamantyl)-1,1,3,3-tetramethyldisiloxane, 1,3-di(1-adamantyl)-1,1,3,3-tetraethyldisiloxane, 1,3-di(1-adamantyl)-1,1,3,3,-tetraphenyldisiloxane and the like.

In the above formula (3), each of $R^9$, $R^{10}$ and $R^{11}$ is a $C_{1-20}$ saturated or unsaturated hydrocarbon group, and may have any of linear, branched chain and cyclic structures. Further, a combination thereof is included in the present invention. If the carbon number exceeds 20, it tends to be difficult to obtain a material such as a corresponding organic halide, or even if it can be obtained, the purity tends to be low in some cases.

Taking stable use in a CVD apparatus into consideration, particularly preferred is a $C_{1-10}$ hydrocarbon group from such a viewpoint that the vapor pressure of the organic silane compound will not be too low.

Examples of the hydrocarbon group for each of $R^9$, $R^{10}$ and $R^{11}$ are not particularly limited, and a $C_{1-20}$, preferably $C_{1-10}$ alkyl group, an aryl group, an arylalkyl group, and an alkylaryl group may be mentioned. $R^9$, $R^{10}$ and $R^{11}$ may be the same or different.

As examples of a case where $R^9$ and $R^{10}$ are not bonded to each other, methyl, ethyl, n-propyl, i-propyl, n-butyl, i-butyl, sec-butyl, tert-butyl, n-pentyl, tert-amyl, n-hexyl, cyclohexyl, phenyl and toluyl groups may, for example, be mentioned.

As examples of a group wherein $R^9$ and $R^{10}$ are bonded to each other and bonded to Si by means of a tertiary carbon, cyclobutyl, cyclobutenyl, cyclopentyl, cyclopentadienyl, cyclohexyl, cyclohexenyl, cyclooctenyl and cyclooctadienyl groups are mentioned as representative examples. Particularly preferred from an economical viewpoint are an iso-propyl group wherein each of $R^9$ and $R^{10}$ is methyl, a sec-butyl group wherein $R^9$ and $R^{10}$ are methyl and ethyl, and cyclopentyl, cyclopentadienyl, cyclohexyl and cyclohexenyl groups wherein $R^9$ and $R^{10}$ are bonded to each other.

$R^{12}$ is a $C_{1-10}$ hydrocarbon group or a hydrogen atom, and the hydrocarbon group is a saturated or unsaturated hydrocarbon group, and may have any of linear, branched chain and cyclic structures. If the carbon number exceeds 10, the vapor pressure of the formed organic silane tends to be low, and its use in a PECVD apparatus tends to be difficult in some cases, such being unfavorable.

Preferred as $R^{12}$ are methyl, ethyl, n-propyl, i-propyl, n-butyl, i-butyl, sec-butyl and tert-butyl which are $C_{1-4}$ hydrocarbon groups, in view of preparation of the material.

d in an integer of from 1 to 3, e is an integer of from 0 to 2, and d+e is an integer of at most 3. Namely, the organic silane compound of the formula (3) is a trialkoxysilane substituted with a hydrocarbon group wherein d=1 and e=0, a dialkoxysilane disubstituted with hydrocarbon groups wherein d=1 and e=1, or d=2 and e=0, or an alkoxysilane trisubstituted with hydrocarbon groups wherein (d=1, e=2), (d=2, e=1) or (d=3, e=0). A mixture thereof is included in the present invention.

Specific examples of the organic silane compound of the formula (3) include:

(G) Iso-propyltrimethoxysilane, diiso-propyldimethoxysilane, triiso-propylmethoxysilane, iso-propylmethyldimethoxysilane, iso-propylethyldimethoxysilane, isopropylphenyldimethoxysilane, iso-propyldimethylmethoxysilane, iso-propyldiethylmethoxysilane and iso-propyldiphenylmethoxysilane, (H) Iso-propyl triethoxysilane, diiso-propyldiethoxysilane, triiso-propylethoxysilane, iso-propylmethyldiethoxysilane, iso-propylethyldiethoxysilane, iso-propylphenyldiethoxysilane, iso-propyldimethylethoxysilane, iso-propyldiethylethoxysilane and iso-propyldiphenylethoxysilane, (I) Sec-butyl trimethoxysilane, disec-butyldimethoxysilane, trisec-butylmethoxysilane, sec-butylmethyldimethoxysilane, sec-butylethyldimethoxysilane, sec-butylphenyldimethoxysilane, sec-butyldimethylmethoxysilane, sec-butyldiethylmethoxysilane and sec-butyldiphenylmethoxysilane, (J) Sec-butyl triethoxysilane, disec-butyldiethoxysilane, trisec-butylethoxysilane, sec-butylmethyldiethoxysilane, sec-butylethyldiethoxysilane, sec-butylphenyldiethoxysilane, sec-butyldimethylethoxysilane, sec-butyldiethylethoxysilane and sec-butyldiphenylethoxysilane, (K) Cyclopentyl trimethoxysilane, dicyclopentyldimethoxysilane, tricyclopentylmethoxysilane, cyclopentylmethyldimethoxysilane, cyclopentylethyldimethoxysilane, cyclopentylphenyldimethoxysilane, cyclopentyldimethylmethoxysilane, cyclopentyldiethylmethoxysilane and cyclopentyldiphenylmethoxysilane, (L) Cyclopentyltriethoxysilane, dicyclopentyldiethoxysilane, tricyclopentylethoxysilane, cyclopentylmethyldiethoxysilane, cyclopentylethyldiethoxysilane, cyclopentylphenyldiethoxysilane, cyclopentyldimethylethoxysilane, cyclopentyldiethylethoxysilane and cyclopentyldiphenylethoxysilane, (M) Cyclopentadienyltrimethoxysilane, dicyclopentadienyldimethoxysilane, tricyclopentadienylmethoxysilane, cyclopentadienylmethyldimethoxysilane, cyclopentadienylethyldimethoxysilane, cyclopentadienylphenyldimethoxysilane, cyclopentadienyldimethylmethoxysilane, cyclopentadienyldiethylmethoxysilane and cyclopentadienyldiphenylmethoxysilane, (N) Cyclopentadienyltriethoxysilane, dicyclopentadienyldiethoxysilane, tricyclopentadienylethoxysilane, cyclopentadienylmethyldiethoxysilane, cyclopentadienylethyldiethoxysilane, cyclopentadienylphenyldiethoxysilane, cyclopentadienyldimethylethoxysilane, cyclopentadienyldiethylethoxysilane and cyclopentadienyldiphenylethoxysilane, (O) Cyclohexyltrimethoxysilane, dicyclohexyldimethoxysilane, tricyclohexylmethoxysilane, cyclohexylmethyldimethoxysilane, cyclohexylethyldimethoxysilane, cyclohexylphenyldimethoxysilane, cyclohexyldimethylmethoxysilane, cyclohexyldiethylmethoxysilane and cyclohexyldiphenylmethoxysilane, (P) Cyclohexyltriethoxysilane, dicyclohexyldiethoxysilane, tricyclohexylethoxysilane, cyclohexylmethyldiethoxysilane, cyclohexylethyldiethoxysilane, cyclohexylphenyldiethoxysilane, cyclohexyldimethylethoxysilane, cyclohexyldiethylethoxysilane and cyclohexyldiphenylethoxysilane, (Q) Cyclohexenyltrimethoxysilane, dicyclohexenyldimethoxysilane, tricyclohexenylmethoxysilane, cyclohexenylmethyldimethoxysilane, cyclohexenylethyldimethoxysilane, cyclohexenylphenyldimethoxysilane, cyclohexenyldimethylmethoxysilane, cyclohexenyldiethylmethoxysilane and cyclohexenyldiphenylmethoxysilane, and (R) Cyclohexenyltriethoxysilane, dicyclohexenyldiethoxysilane, tricyclohexenylethoxysilane, cyclohexenylmethyldiethoxysilane, cyclohexenylethyldiethoxysilane, cyclohexenylphenyldiethoxysilane, cyclohexenyldimethylethoxysilane, cyclohexenyldiethylethoxysilane and cyclohexenyldiphenylethoxysilane.

The method for producing the organic silane compound of the above formula (1) is not particularly limited. For example, the organic silane compound of the formula (1) can be produced by reacting organic lithium having a tertiary carbon atom and a lithium atom directly bonded to each other, produced by reacting an organic halide of the following formula (4):

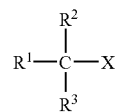

wherein each of $R^1$ to $R^3$ is as defined above, and X is a chlorine atom, a bromine atom or an iodine atom, with metal lithium particles, with a halogenated alkoxysilane (m=1–3) or a tetraalkoxysilane (m=0) of the following formula (5):

$$X'_m Si(OR^4)_{4-m} \qquad (5)$$

wherein $R^4$ is as defined above, X' is a fluorine atom, a chlorine atom, a bromine atom or an iodine atom, and m is an integer of from 0 to 3. Examples of the organic halide of the formula (4) include tert-butyl chloride, tert-butyl bromide, tert-butyl iodide, tert-amyl chloride, tert-amyl bromide, tert-amyl iodide, 1-adamantyl chloride, 1-adamantyl bromide, 1-adamantyl iodide, 1-twistyl chloride, 1-twistyl bromide, 1-twistyl iodide, 1-diamantyl chloride, 1-diamantyl bromide, 1-diamantyl iodide, 1-triptycyl chloride, 1-triptycyl bromide and 1-triptycyl iodide.

Examples of the halogenated alkoxysilane or tetraalkoxysilane of the formula (5) include chlorotrimethoxysilane, dichlorodimethoxysilane, trichloromethoxysilane, tetramethoxysilane, chlorotriethoxysilane, dichlorodiethoxysilane, trichloroethoxysilane, tetramethoxysilane, tetraethoxysilane, tetrapropoxysilane, chlorotri-i-propoxysilane, dichlorodi-i-propoxysilane, trichloro-i-propoxysilane, tetra-i-propoxysilane, tetrabutoxysilane, tetra-i-butoxysilane, tetra-sec-butoxysilane and tetra-tert-butoxysilane.

By employing the present production method, high purity organic silane compound of the formula (1) can be obtained with a high percentage of yield while suppressing formation of by-products. Particularly, an organic silane compound having at least two structures in which a tertiary carbon atom is directly bonded to a silicon atom, can be produced, which can hardly be produced industrially by other production methods of using e.g. organic magnesium.

The conditions of the reaction of the organic halide of the above formula (4) and metal lithium particles are not particularly limited, and one example is shown below.

As the metal lithium to be used, e.g. a lithium wire, a lithium ribbon or a lithium shot may, for example, be employed, and it is preferred to employ lithium fine particles having a particle size of at most 500 μm in view of reaction efficiency.

The solvent to be used for the reaction of the organic halide with the metal lithium particles is not particularly limited so long as it is used for said technical field. For example, a saturated hydrocarbon such as n-pentane, i-pentane, n-hexane, cyclohexane, n-heptane or n-decane, an unsaturated hydrocarbon such as toluene, xylene or decene-1, or an ether such as diethyl ether, propyl ether or dibutyl ether may be used.

The reaction temperature for the reaction of the organic halide with the metal lithium particles is preferably such a temperature range that the formed organic lithium having a tertiary carbon atom and lithium are directly bonded to each other will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The prepared organic lithium having a tertiary carbon atom and a lithium atom directly bonded to each other may be used as it is after the production, or it may be used after unreacted organic halide and metal lithium, and lithium halide as a reaction by-product are removed.

The conditions of the reaction of the organic lithium having a tertiary carbon atom and a lithium atom directly bonded to each other and the halogenated alkoxysilane or tetraalkoxysilane of the above formula (3), are not particularly limited, and one example is shown below.

The reaction solvent to be used may be the same solvent as one used for the above reaction of the organic halide with the metal lithium particles. The reaction temperature is preferably such a temperature range that the organic lithium having a tertiary carbon atom and lithium directly bonded to each other to be used will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The method for producing the organic silane of the above formula (2) is not particularly limited. For example, a dialkoxysilane disubstituted with hydrocarbon groups of the following formula (9) which is the compound of the above formula (2) wherein b=1 and c=0:

(9)

wherein each of $R^5$, $R^7$ and $R^8$ is as defined for the above formula (2), or an alkoxysilane trisubstituted with hydrocarbon groups of the following formula (10) which is the compound of the formula (2) wherein b=0 and c=0:

(10)

wherein each of $R^5$, $R^7$ and $R^8$ is as defined for the above formula (2), can be produced by reacting an organic lithium compound or an organic magnesium compound of the following formula (11):

(11)

wherein $R^5$ is as defined for the above formula (2), and M is Li, MgCl, MgBr or MgI, with a halogenated silane substituted with a hydrocarbon group or an alkoxysilane substituted with a hydrocarbon group of the following formula (12):

$$Z_f SiR^5{}_g[(O)_b R^7]_h (OR^8)_{4-(f+g+h)} \qquad (12)$$

wherein each of $R^5$, $R^7$, $R^8$ and b is as defined for the above formula (2), Z is a fluorine atom, a chlorine atom, a bromine atom or an iodine atom, f is an integer of from 0 to 3, g is an integer of from 0 to 2, h is an integer of from 0 to 2 when b=0, or an integer of from 0 to 4 when b=1, and f+g+h is from 0 to 4.

The method for producing a disiloxane hexa-substituted with hydrocarbon groups of the above formula (2) wherein c=1 is not particularly limited, and it can be produced by dimerization of the obtained dialkoxysilane disubstituted with hydrocarbon groups or alkoxysilane trisubstituted with hydrocarbon groups in the presence of water and an acid.

Further, after the preparation reaction, in a case where a halogen atom directly bonded to silicon remains in the alkoxysilane substituted with a hydrocarbon group as a reaction product, an alkali metal alkoxide of the following formula (13):

$$R^8 OM' \qquad (13)$$

wherein M' is an alkali metal, and $R^8$ is as defined for the above formula (2), may be reacted therewith for alkoxylation.

Examples of the alkali metal alkoxide of the above formula (13) include lithium methoxide, lithium ethoxide, lithium-i-propoxide, sodium methoxide, sodium ethoxide, sodium-i-propoxide, potassium methoxide, potassium ethoxide and potassium-i-propoxide.

By employing the present production method, high purity organic silane compound of the formula (1) can be obtained with a high percentage of yield while suppressing formation of by-products.

The organic lithium compound or organic magnesium compound of the above formula (11) used for production can be produced by reacting an organic halide with metal lithium particles or metal magnesium.

The conditions of the reaction of the organic halide with metal lithium particles or metal magnesium to prepare the organic lithium compound or organic magnesium compound of the above formula (11) are not particularly limited, and one example is shown below.

As the metal lithium to be used, a lithium wire, a lithium ribbon or a lithium shot may, for example, be employed, and it is preferred to employ lithium fine particles having a particle size of at most 500 μm in view of reaction efficiency.

As the metal magnetism to be used, magnesium ribbon, magnesium particles or magnesium powder may, for example, be used.

The solvent to be used for the above reaction is not particularly limited so long as it is used in said technical field, and for example, a saturated hydrocarbon such as n-pentane, i-pentane, n-hexane, cyclohexane, n-heptane or n-decane, an unsaturated hydrocarbon such as toluene, xylene or decene-1, or an ether such as diethyl ether, dipropyl ether, tert-butyl methyl ether, dibutyl ether or cyclopentyl methyl ether may be used. Further, a solvent mixture thereof may also be used.

The reaction temperature for the above reaction is preferably such a temperature range that the formed organic lithium or organic magnesium will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The prepared organic lithium or organic magnesium may be used as it is after prepration, or may be used after unreacted organic halide and metal lithium or metal magnesium, and lithium halide or magnesium halide as a reaction by-product are removed.

The conditions of the reaction of the organic lithium or organic magnesium with the halogenated silane substituted with a hydrocarbon group or alkoxysilane substituted with a hydrocarbon group of the above formula (12) are not particularly limited, and one example is shown below.

The reaction solvent to be used may be the same solvent as one used for the above reaction of the organic halide with metal lithium or metal magnesium. The reaction temperature is preferably such a temperature range that the organic lithium or organic magnetism to be used will not decompose. The reaction is carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The reaction condition of the alkali metal alkoxide of the above formula (13) in the case where a halogen atom directly bonded to silicon remains, are not particularly limited, and the reaction can be carried out under the same conditions of the above reaction of the organic lithium or organic magnesium with the halogenated alkoxysilane or tetraalkoxysilane.

The method for producing the organic silane compound of the above formula (3) is not particularly limited. For example, the organic silane compound of the formula (3) can be produced by reacting a compound having a secondary carbon atom and a lithium atom directly bonded to each other, produced by reacting an organic compound of the following formula (6):

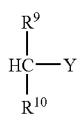

(6)

wherein each of $R^9$ and $R^{10}$ is as defined above, and Y is a hydrogen atom, a chlorine atom, a bromine atom or an iodine atom, with organic lithium or metal lithium particles, with a halogenated silane, a halogenated alkoxysilane or a tetraalkoxysilane of the following formula (7):

$$Y'_pSiR^{11}_q(OR^{12})_{4-(p+q)} \quad (7)$$

wherein Y' is a fluorine atom, a chlorine atom, a bromine atom or an iodine atom, each of $R^{11}$ and $R^{12}$ is as defined above, p is an integer of from 0 to 4, q is an integer of from 0 to 2, and p+q is an integer of at most 4.

Further, with respect to the above production method, a method for producing the organic silane compound of the formula (3) by using metal magnesium instead of the organic lithium or metal lithium particles is also included in the present invention.

Examples of the organic compound of the formula (6) wherein Y is a chlorine atom, a bromine atom or an iodine atom include iso-propyl chloride, iso-propyl bromide, iso-propyl iodide, sec-butyl chloride, sec-butyl bromide, sec-butyl iodide, cyclopentyl chloride, cyclopentyl bromide, cyclopentyl iodide, cyclohexyl chloride, cyclohexyl bromide and cyclohexyl iodide.

Further, examples of the organic compound of the formula (6) wherein Y is a hydrogen atom include cyclopentadiene, pentamethylcyclopentadiene and 1,2,3,4-tetramethyl-1,3-cyclopentadiene, and by reacting organic lithium such as n-butyl lithium or tert-butyl lithium with such a compound, a compound having a secondary carbon atom and a lithium atom directly bonded to each other can be produced.

Examples of the halogenated silane, halogenated alkoxysilane or tetraalkoxysilane of the formula (7) include tetrachlorosilane, chlorotrimethoxysilane, dichlorodimethoxysilane, trichloromethoxysilane, tetramethoxysilane, chlorotriethoxysilane, dichlorodiethoxysilane, trichloroethoxysilane, tetramethoxysilane, tetraethoxysilane, tetrapropoxysilane, chlorotri-i-propoxysilane, dichlorodi-i-propoxysilane, trichloro-i-propoxysilane, tetra-i-propoxysilane, tetrabutoxysilane, tetra-i-butoxysilane, tetra-sec-butoxysilane, tetra-tert-butoxysilane, methyltrimethoxysilane, dimethyldimethoxysilane, ethyltrimethoxysilane, diethyldiethoxysilane, vinyltriethoxysilane, vinyltrimethoxysilane, vinyltrichlorosilane, divinyldichlorosilane, phenyltrimethoxysilane and diphenyldimethoxysilane.

Further, after the preparation reaction, in a case where a halogen atom directly bonded to silicon remains in the alkoxysilane substituted with a hydrocarbon group as a reaction product, an alkali metal alkoxide of the following formula (8):

$$R^{12}OM \quad (8)$$

wherein M is an alkali metal, and $R^{12}$ is as defined above, may be reacted for alkoxylation.

Examples of the alkali metal alkoxide of the above formula (8) include lithium methoxide, lithium ethoxide, lithium-i-propoxide, sodium methoxide, sodium ethoxide, sodium-i-propoxide, potassium methoxide, potassium ethoxide and potassium-i-propoxide.

By employing the present production method, high purity organic silane compound of the formula (3) can be obtained with a high percentage of yield while suppressing the formation of by-products.

The conditions for production of the compound having a secondary carbon atom and a lithium atom (or a magnesium atom) directly bonded to each other are not particularly limited, and one example is shown below.

As the metal lithium to be used, a lithium wire, a lithium ribbon or a lithium shot may, for example, be employed, and it is preferred to employ lithium fine particles having a particle size of at most 500 μm in view of reaction efficiency.

As the metal magnetism to be used, magnesium ribbon, magnesium particles or magnetism powder may, for example, be employed.

As the organic lithium to be used, a n-hexane solution of n-butyllithium or n-pentane solution of tert-butyllithium may, for example, be used.

The solvent to be used for the above reaction is not particularly limited so long as it is used in said technical field. For example, a saturated hydrocarbon such as n-pentane, i-pentane, n-hexane, cyclohexane, n-heptane or n-decane, an unsaturated hydrocarbon such as toluene, xylene or decene-1, or an ether such as diethyl ether, dipropyl ether, tert-butyl methyl ether, dibutyl ether or cyclopentyl methyl ether may be used. Further, a solvent mixture thereof may also be used.

The reaction temperature for the above reaction is preferably such a temperature range that the formed compound having a secondary carbon atom and a lithium atom bonded to each other, or compound having a secondary carbon atom and a magnesium atom directly bonded to each other, will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The prepared compound having a secondary carbon atom and a lithium atom directly bonded to each other or compound having a secondary carbon atom and a magnesium atom directly bonded to each other, may be used as it is after the production, or it may be used after unreacted organic halide and metal lithium or metal magnesium, and lithium halide or magnesium halide as a reaction by-product are removed.

The conditions of the reaction of the compound having a secondary carbon atom and a lithium atom directly bonded to each other or the compound having a secondary carbon atom and a magnesium atom directly bonded to each other, thus obtained, with the halogenated silane, halogenated alkoxysilane or tetraalkoxysilane of the above formula (3), are not particularly limited, and one example is shown below.

The reaction solvent to be used may be the same solvent as one used for the above reaction of the compound having a secondary carbon atom and a lithium atom (or a magnesium atom) directly bonded to each other. The reaction temperature is preferably such a temperature range that the compound having a secondary carbon atom and a lithium atom (or a magnesium atom) directly bonded to each other will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

As a purification method of the formed organic silane compound of each of the formulae (1) to (3), in order to achieve a water content of less than 50 ppm and an amount of impurities derived from production materials, other than the elements of silicon, carbon, oxygen and hydrogen, of less than 10 ppb, which are effective for use as an insulating film material, lithium salt, magnesium salt and alkali metal salt which are by-products should be removed by means such as filtration by using a glass filter, a sintered porous body or the like, distillation under normal pressure or reduced pressure, or purification by column separation using silica, alumina or high polymer gel. At this time, these means may be combined as the case requires. In a method of extracting lithium salt, magnesium salt and alkali metal salt which are by-products with e.g. water, which has been employed in a conventional organic synthesis technology, the finally obtained organic silane compound of the formula (1) has a large amount of moisture and impurities other than the elements of silicon, carbon, oxygen and hydrogen, particularly metal impurity residue, and is inappropriate as an insulating film material in some cases.

Further, in a case where a by-product containing a silanol structure is formed, hydroxyl groups of the silanol are precipitated in a form of a sodium salt or a potassium salt with e.g. sodium hydride or potassium hydride, and then the alkoxysilane substituted with a hydrocarbon group as the main product can be isolated by distillation.

For production, the operation is carried out in accordance with a method in the field of said organic metal compound prepration. Namely, it is preferred that the reaction is carried out in an atmosphere of dehydrated and deoxidized nitrogen or argon, and a solvent, a column bulking agent for purification, etc., to be used are preliminarily subjected to dehydration operation. Further, it is preferred that impurities such as metal residue and particles are removed.

The organic silane compounds of the formulae (1) to (3) of the present invention are materials suitable as a low-dielectric constant insulating material for film formation by a PECVD apparatus.

It is also possible to obtain a low-dielectric constant insulating material having a decreased dielectric constant in such a manner that the above material is formed into a film by CVD, followed by heat treatment at a temperature of at least 350° C. at which the tertiary carbon atom and the silicon atom are separated, and the separated hydrocarbon molecule is discharged out of the film to purposely form pores of a molecule size in the film so that the film becomes porous.

The low-dielectric constant insulating film material of the present invention is suitable for production of ULSI employing multilevel interconnection, and the present invention further provides a semiconductor device employing the insulating film.

Now, the present invention will be described in detail with reference to Examples. However, it should be understood that the present invention is by no means restricted to such specific Examples.

EXAMPLE 1

Preparation of Organic Lithium Having a Tertiary Carbon Atom and a Lithium Atom Directly Bonded to Each Other 1.40 g (0.200 mol) of Li particles having an average particle size of 150 um and 100 ml of dry pentane were charged in a 200 ml Schlenk tube reactor equipped with a dropping funnel in a stream of nitrogen, and a solution having 21.5 g (0.100 mol) of 1-bromoadamantane dissolved in 50 ml of n-pentane was dropwise added thereto from the dropping funnel with stirring at 30° C. while keeping the internal temperature at 30° C., followed by stirring for 14 hours under reflux of n-pentane.

After completion of the reaction, unreacted metal Li and by-product LiBr were removed by filtration to obtain a n-pentane solution of 1-adamantyl lithium.

Preparation of Organic Silane Compound Having Such a Structure that a Tertiary Carbon Atom is Directly Bonded to a Silicon Atom 50 ml of dry pentane and 13.7 g (0.090 mol) of tetramethoxysilane were charged in a 200 ml Schlenk tube reactor equipped with a dropping funnel, and the above prepared n-pentane solution of 1-adamantyl lithium was dropwise added thereto from the dropping funnel while keeping the internal temperature at 0° C. After completion of the dropwise addition, stirring was carried out at room temperature for 2 hours. After completion of the reaction, n-pentane was distilled off, and the aimed product 1-adamantyltrimethoxysilane was purified by isolation by means of column chromatography. The percentage of yield was 82%.

EXAMPLE 2

The same operation as in Example 1 was carried out except that 6.85 g (0.045 mol) of tetramethoxysilane was used instead of 13.7 g (0.090 mol) to obtain the aimed product di(1-adamantyl)dimethoxysilane. The percentage of yield was 71%.

Comparative Example 1

Preparation of Organic Magnesium Having a Tertiary Carbon Atom and a Lithium Atom Directly Bonded to Each Other 21.4 g (0.880 mol) of magnesium and 125.0 g (0.960 mol) of dibutyl ether were charged in a 1,000 ml flask equipped with a reflux condenser, a dropping funnel and a stirring apparatus, in an atmosphere of nitrogen, and after stirring was started, a solution having 172.1 g (0.800 mol) of 1-bromoadamantane and 4.36 g (0.0400 mol) of ethyl bromide diluted with 250.0 g (1.92 mol) of dibutyl ether was dropwise added thereto from the dropping funnel over a period of 2 hours under reflux of dibutyl ether, and then stirring was carried out for 4 hours under reflux of dibutyl ether, to obtain a dibutyl ether solution of 1-adamantyl magnesium bromide.

Preparation of Organic Silane Compound Having Such a Structure that a Tertiary Carbon is Directly Bonded to a Silicon Atom 200 ml of dry dibutyl ether and 54.8 g (0.360 mol) of tetramethoxysilane were charged in a 2,000 ml reactor equipped with a reflux condenser and a stirring apparatus in an atmosphere of nitrogen, and the above prepared dibutyl ether solution of 1-adamantyl magnesium bromide was dropwise added thereto by a rotary pump while keeping the internal temperature at 0° C. After completion of the dropwise addition, stirring was carried out at room temperature for 2 hours.

The product was confirmed by means of gas chromatography, whereupon no formation of the aimed product di(1-adamantyl)dimethoxysilane was confirmed. Stirring was further carried out for 2 hours under reflux of dibutyl ether, but no formation of di(1-adamantyl)dimethoxysilane was confirmed.

EXAMPLE 3

Preparation of Organic Lithium Having a Tertiary Carbon Atom and a Lithium Atom Directly Bonded to Each Other 1.39 g (0.200 mol) of Li particles having an average particle size of 75 µm and 50 ml of dry pentane were charged in a 200 ml Schlenk tube reactor equipped with a reflux condenser and a dropping funnel in a stream of argon, and a solution having 3.41 g (0.020 mol) of 1-chloroadamantane dissolved in 50 ml of n-pentane was dropwise added thereto from the dropping funnel with stirring at 30° C. while keeping the internal temperature at 30° C. Stirring was carried out further for 8 hours under reflux of n-pentane, and then it was confirmed that no 1-chloroadamantane as the material was detected, and a n-pentane solution of 1-adamantyl lithium was obtained.

Preparation of Organic Silane Compound Having Such a Structure that a Tertiary Carbon Atom is Directly Bonded to a Silicon Atom 50 ml of dry n-pentane and 3.33 g (0.016 mol) of tetraethoxysilane were charged in a 200 ml Schlenk tube reactor equipped with a reflux condenser and a dropping funnel in an atmosphere of argon, and the above prepared n-pentane solution of 1-adamantyl lithium was dropwise added thereto from the dropping funnel at room temperature. After completion of the dropwise addition, stirring was carried out for 5 hours under reflux of n-pentane. After completion of the reaction, n-pentane was distilled off, and the aimed product 1-adamantyltriethoxysilane was purified by isolation by means of column chromatography. The percentage of yield was 72%.

EXAMPLE 4

The same operation as in Example 3 was carried out except that 2.44 g (0.016 mol) of tetramethoxysilane was used instead of tetraethoxysilane to obtain the aimed product 1-adamantyltrimethoxysilane. The percentage of yield was 78%.

Comparative Example 2

Preparation of Organic Magnesium Having a Tertiary Carbon Atom and a Magnesium Atom Directly Bonded to Each Other 2.92 g (0.120 mol) of magnesium and 30 ml of dibutyl ether were charged in a 200 ml Schlenk tube equipped with a reflux condenser, a dropping funnel and a stirring apparatus in an atmosphere of nitrogen, and a solution having 21.5 g (0.100 mol) of 1-bromoadamantane and 1.09 g (0.0100 mol) of ethyl bromide dissolved in 40 ml of dibutyl ether was dropwise added thereto from the dropping funnel at 80° C. over a period of 1 hour, and stirring was carried out further for 2 hours at 120° C. to obtain a dibutyl ether solution of 1-adamantyl magnesium bromide.

Preparation of Organic Silane Compound Having such a Structure that a Tertiary Carbon Atom is Directly Bonded to a Silicon Atom To the above dibutyl ether solution of 1-adamantyl magnesium bromide in the 200 ml Schlenk tube, a solution having 16.7 g (0.080 mol) of tetraethoxysilane dissolved in 20 ml of dry dibutyl ether was dropwise added from the dropping funnel at 45° C. over a period of 10 minutes. After completion of the dropwise addition, stirring was carried out at 120° C. for 6 hours.

The reaction liquid was analyzed by means of a gas chromatography mass spectrometer (GC-MS), and no formation of 1-adamantyltriethoxysilane or di(1-adamantyl)diethoxysilane was confirmed at all.

EXAMPLE 5

Preparation of Organic Silane Compound Having Such a Structure that a Tertiary Carbon Atom is Directly Bonded to a Silicon Atom 50.0 g (0.240 mol) of tetraethoxysilane and 250 ml of n-pentane were charged in a 500 ml four-necked flask reactor equipped with a reflux condenser, a dropping funnel and a stirring apparatus in an atmosphere of nitrogen, and cooled to 0° C. 78.0 g (0.289 mol) of a n-pentane solution of 23.7 wt % tert-butyllithium was dropwise added thereto from the dropping funnel over a period of 1 hour, and stirring was carried out further for 2 hours.

The percentage of yield of tert-butyltriethoxysilane was 93.0% by a gas chromatography internal standard method.

Lithium ethoxide was removed by filtration from the reaction liquid, and n-pentane was distilled off from the filtrate, followed by distillation under reduced pressure to isolate tert-butyltriethoxysilane. The yield was 39.6 g, and the percentage of isolated yield was 74.8%.

The results of analysis of the isolated tert-butyltriethoxysilane by $^1$H-NMR, $^{13}$C-NMR and GC-MS were as follows, and it was shown that the aimed product had a high purity.

$^1$H-NMR (CDCl$_3$): 1.025 ppm (s, 9H), 1.285 ppm (t, 9H) 3.915 ppm (q, 6H)

$^{13}$C-NMR (CDCl$_3$) 17.583 ppm, 18.426 ppm, 26.391 ppm, 58.785 ppm

GC-MS: Mw=220, C$_{10}$H$_{24}$O$_3$Si

Further, the water content and the lithium content in 100 g of the obtained tert-butyltriethoxysilane were measured by means of a Karl Fischer moisture meter and ICP-MS (inductively coupled plasma mass spectrometer, manufactured by Yokogawa Analytical Systems, Inc., tradename "HP4500") and as a result, H$_2$O=17 ppm and Li<10 ppb, and the obtained product was useful as an insulating film material.

Comparative Example 3

Preparation of an Organic Silane Compound Having Such a Structure that a Tertiary Carbon Atom is Directly Bonded to a Silicone Atom 11.8 g (0.0567 mol) of tetraethoxysilane and 50 ml of tetrahydrofuran were charged in a 500 ml four-necked flask reactor equipped with a reflux condenser, a dropping funnel and a stirring apparatus in an atmosphere of nitrogen, and cooled to 0° C. 40 ml (0.0680 mol) of a tetrahydrofuran solution of 1.70 mol/L tert-butyl magnesium chloride was dropwise added thereto from the dropping funnel over a period of 1 hour, and stirring was carried out for 2 hours. Part of the reaction liquid was collected to carry out gas chromatography, but no formation of tert-butyltriethoxysilane was confirmed.

Stirring was carried out further for 3 hours at room temperature to conduct reaction, but no formation of tert-butyltriethoxysilane was confirmed.

Stirring was carried out further for 3 hours under reflux of tetrahydrofuran to conduct reaction. The percentage of yield of tert-butyltriethoxysilane was 1.4% by a gas chromatography internal standard method, and it was found that the aimed product can not efficiently be prepared by the reaction of tert-butyl magnesium chloride with tetraethoxysilane.

EXAMPLE 6

Preparation of Organic Silane Compound Having Such a Structure that a Tertiary Carbon Atom is Directly Bonded to a Silicon Atom The same operation as in Example 5 was carried out except that 36.6 g (0.240 mol) of tetramethoxysilane was used instead of tetraethoxysilane to obtain the aimed product tert-butyltrimethoxysilane. As a result, the percentage of yield of tert-butyltrimethoxysilane was 91.1% by a gas chromatography internal standard method, and the percentage of isolated yield by distillation under reduced pressure was 70.0%.

The results of analysis of the isolated tert-butyltrimethoxysilane by $^1$H-NMR, $^{13}$C-NMR and GC-MS were as follows, and it was shown that the aimed product had a high purity.

$^1$H-NMR (CDCl$_3$): 1.043 ppm (s, 9H), 3.683 ppm (s, 9H)

$^{13}$C-NMR (CDCl$_3$): 17.876 ppm, 26.410 ppm, 51.277 ppm

GC-MS: Mw=178, C$_7$H$_{18}$O$_3$Si

Further, the water content and the lithium content in the obtained tert-butyltrimethoxysilane were measured by means of a Karl Fischer moisture meter and ICP-MS and as a result, H$_2$O=14 ppm and Li<10 ppb, and the obtained product was useful as an insulating film material.

EXAMPLE 7

The same operation as in Example 3 was carried out except that the aimed product 1-adamantyltriethoxysilane was purified by isolation by means of distillation under reduced pressure instead of column chromatography, to obtain the aimed product 1-adamantyltriethoxysilane. The percentage of yield was 74.0%.

The results of analysis of the isolated 1-adamantyltriethoxysilane by $^1$H-NMR, $^{13}$C-NMR and GC-MS were as follows, and it was shown that the aimed product had a high purity.

$^1$H-NMR (CDCl$_3$): 1.290 ppm (t, 9H), 1.836 ppm and 1.886 ppm (two peaks, 15H), 3.890 ppm (q, 6H)

$^{13}$C-NMR (CDCl$_3$): 18.499 ppm, 22.656 ppm, 27.453 ppm, 36.975 ppm, 37.616 ppm, 58.785 ppm GC-MS: Mw=298, C$_{16}$H$_{30}$O$_3$Si Further, the water content and the lithium content in the obtained 1-adamantyltriethoxysilane were measured by means of a Karl Fischer moisture meter and ICP-MS and as a result, H$_2$O=10 ppm and Li<10 ppb, and the obtained product was useful as an insulating film material.

EXAMPLE 8

Film Formation by Plasma Polymerization of tert-butyltrimethoxysilane

Figure 2:
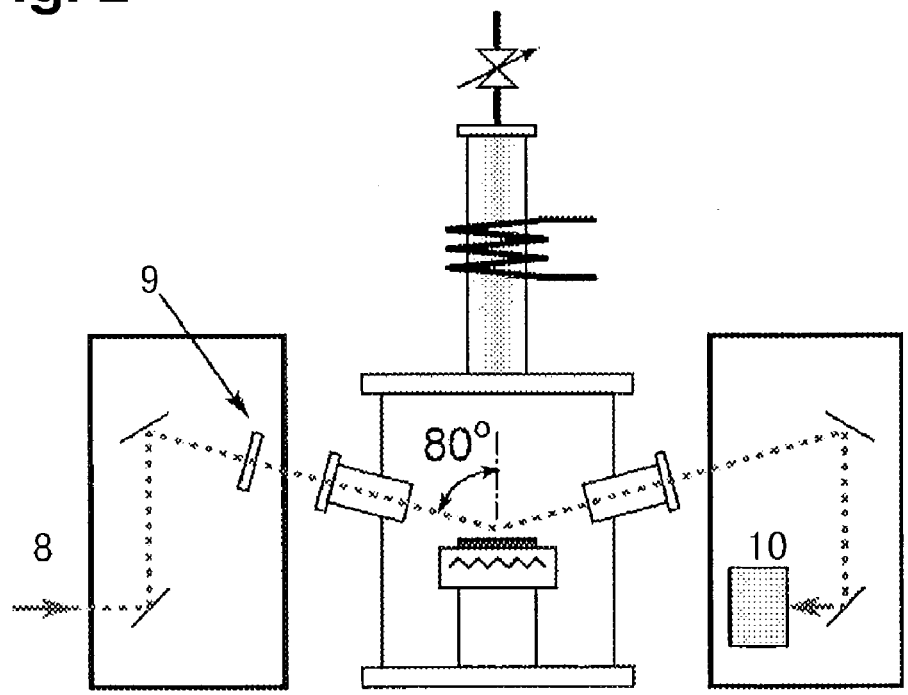
FIG. 2 is a schematic view illustrating the constitution of IRRAS.

For preparation of a thin film, an inductively coupled remote plasma enhanced CVD apparatus (PECVD apparatus) as shown in FIG. 1 was used. This apparatus mainly comprises a plasma source 1 made of quartz glass, a film formation chamber 2, a carburetor 3, a vacuum exhaust apparatus 4, a silicon substrate 5, a high frequency power source 6 and a matching network 7, and the film formation chamber 2 is equipped with a high sensitive infrared reflection absorption spectroscope (IRRAS) as shown in FIG. 2. The IRRAS is an apparatus to confirm the film formation state of a polymer film in such a manner that infrared light 8 is polarized by a polarizing plate 9 and irradiated on a polymer film to be deposited on the silicon substrate 5 at an angle of incidence of 80°, and the reflected light from the polymer film is detected by a mercury/cadmium/tellurium semiconductor infrared sensor 10. By using this apparatus, film formation by plasma polymerization of the tert-butyltrimethoxysilane prepared in Example 6 was carried out as follows.

The film formation chamber 2 was evacuated of air to at most 10$^{-4}$ Pa, and then 5 sccm of oxygen gas was introduced, and the exhaust velocity was adjusted by an orifice valve so that the pressure in the chamber would be 10 Pa. Then, the oxygen gas was eliminated, and a tert-butyltrimethoxysilane gas as the material was introduced to the film formation chamber 2 through the carburetor 3 until the internal pressure would be 10 Pa. After the internal pressure was stabilized, a high frequency of 75 W was applied to the plasma source 1 to generate plasma, and a thin film was deposited on the silicon substrate 5 installed in the film formation chamber 2. During this time, the flow rate of the tert-butyltrimethoxysilane gas was kept at 5 sccm, and film formation was carried out for 12 minutes.

By measurement by the IRRAS at the time of film formation, it was confirmed that a polymer of silicon oxide having such a structure that a tertiary butyl group was directly bonded to a silicon atom was deposited.

The obtained thin film by plasma polymerization on the silicon substrate was analyzed by means of an electron microscope (SEM), a X-ray photoelectron spectroscope (XPS) and an infrared absorption spectroscope (IR), and the results are shown below.

Film thickness (SEM): 120 nm

Film formation (XPS): C=37 atom %, O=49 atom % and Si=14 atom %

C/Si=2.64

Infrared ray absorption (IR): Tertiary butyl group directly bonded to a silicon atom (2,956 cm$^{-1}$, 1,479 cm$^{-1}$, 727 cm$^{-1}$), methyl group directly bonded to a silicon atom (2,853 cm$^{-1}$, 1,273 cm$^{-1}$, 798 cm$^{-1}$)

Comparative Example 4

Film Formation by Plasma Polymerization of Methyltrimethoxysilane

A thin film by plasma polymerization was formed on a silicon substrate in the same manner as in Example 8 except that methyltrimethoxysilane was used instead of tert-butyltrimethoxysilane, and the film formation time by polymerization was 20 minutes. The results of analysis are shown below.

IRRAS: Deposition of the polymer of silicon oxide having such a structure that a methyl group was directly bonded to a silicon atom was confirmed.

Film thickness (SEM): 22 nm

Film composition (XPS): C=37 atom %, O=43 atom % and Si=20 atom % C/Si=1.85

Infrared absorption (IR): Methyl group directly bonded to a silicon atom (2,853 cm$^{-1}$, 1,273 cm$^{-1}$, 798 cm$^{-1}$), hydrogen directly bonded to a silicon atom (broad peak in the vicinity of 2,300 cm$^{-1}$) and hydroxyl group directly bonded to a silicon atom (broad peak in the vicinity of 3,300 cm$^{-1}$)

It was confirmed that the film formation rate was slow, the amount of carbon uptake was small, and a polymer thin film having a hydroxyl group and hydrogen directly bonded to silicon, which was inappropriate as an insulating film, was obtained, as compared with Example 8.

As mentioned above, it was found that by plasma polymerization of tert-butyltrimethoxysilane alone, a silicon oxide polymer thin film having both tertiary butyl group and methyl group directly bonded to a silicon atom, having a high carbon content, useful as an insulating film, can be obtained at a high film formation rate as compared with a conventional method.

EXAMPLE 9

Preparation of tert-butyldimethylchlorosilane 258.2 g (2.00 mol) of dimethyldichlorosilane and 600 ml of n-pentane were charged in a 3 L four-necked flask reactor equipped with a reflux condenser, a dropping funnel and a stirring apparatus, in an atmosphere of nitrogen, and cooled to 0° C. 539.6 g (2.00 mol) of a n-pentane solution of 23.7 wt % tert-butyllithium was dropwise added thereto from the dropping funnel over a period of 1 hour, and stirring was carried out for 2 hours.

After the reaction, by-product lithium chloride was removed by filtration, and n-pentane was distilled off from the filtrate, and then tert-butyldimethylchlorosilane as a purified product was isolated by distillation. The yield was 235.1 g, and the percentage of isolated yield was 78.0%.

Preparation of tert-butyldimethylethoxysilane 156.9 g (1.04 mol) of tert-butyldimethylchlorosilane, 82.3 g (1.16 mol) of sodium ethoxide having a purity of 96% and 1.6 L of n-hexane were charged in a 2 L separable flask reactor equipped with a stirring apparatus in a stream of nitrogen, and reaction was carried out for 22 hours under reflux of n-hexane.

The solid residue was collected by filtration by means of a glass filter to obtain a reaction mixture solution. Analysis was carried out by means of gas chromatography, whereupon the percentage of yield of the aimed product tert-butyldimethylethoxysilane was 66.8%, and the percentage of yield of by-product tert-butyldimethylhydroxysilane was 33.2%.

Removal of By-product and Purification of tert-butyldimethylethoxysilane

The above obtained reaction mixture was charged in a 2 L separable flask reactor equipped with a stirring apparatus in a stream of nitrogen, and 16.6 g (0.691 mol) of sodium hydride was added thereto, followed by stirring at room temperature for 1 hour. Analysis by gas chromatography was carried out, whereupon the amount of by-product tert-butyldimethylhydroxysilane was at most detection limit.

After completion of the reaction, the solid residue was collected by filtration by means of a glass filter to obtain a reaction mixture solution. n-Hexane was distilled off from the reaction mixture solution, and the aimed product tert-butyldimethylethoxysilane was isolated by distillation at normal pressure.

The yield was 91.5 g (0.572 mol), corresponding to a percentage of yield of 55.0%.

The results of analysis of the isolated tert-butyldimethylethoxysilane by means of $^1$H-NMR, $^{13}$C-NMR and GC-MS were as follows.

$^1$H-NMR: 0.079 ppm (s, 6H), 1.01 ppm (s, 9H), 1.13 ppm (t, 3H), 3.56 ppm (q, 2H)

$^{13}$C-NMR: 18.23 ppm, 18.66 ppm, 25.92 ppm, 58.51 ppm

GC-MS: Mw=160, $C_8H_{20}OSi$

Further, the water content and the sodium and lithium contents in 100 g of the obtained tert-butyldimethylethoxysilane were measured by means of a Karl Fischer moisture meter and ICP-MS (inductively coupled plasma mass spectrometer, manufactured by Yokogawa Analytical System, Inc., tradename "HP-4500") and as a result, $H_2O$=10 ppm, Na<10 ppb and Li<10 ppb, and the obtained product was useful as an insulating film material.

Comparative Example 5

The same operation as in Example 1 was carried out except that after the reaction of tert-butyldimethylchlorosilane with sodium ethoxide of Example 9, sodium chloride and unreacted sodium ethoxide were not removed by filtration, but water was added to carry out removal of the solution by separation and extraction, and further, by-product tert-butyldimethylhydroxysilane was not removed by the reaction with sodium hydride, to prepare tert-butyldimethylethoxysilane.

The water content and the sodium content in the obtained tert-butyldimethylethoxysilane were measured by means of a Karl Fischer moisture meter and ICP-MS, whereupon $H_2O$=210 ppm and Na=98 ppm, and the obtained product was inappropriate as an insulating film material.

EXAMPLE 10

Preparation of Organic Lithium Having a Secondary Carbon Atom and a Lithium Atom Directly Bonded to Each Other 15.8 g (239 mmol) of cyclopentadiene obtained by cracking distillation of dicyclopentadiene and 50 ml of dry tetrahydrofuran were charged in a 200 ml Schlenk tube reactor equipped with a dropping funnel and a stirring apparatus in a stream of nitrogen, and cooled to –20° C. 90.0 ml (239 mmol) of 2.66 mol/L n-butyllithium was dropwise added thereto with stirring over a period of 45 minutes, and reaction was carried out at –20° C. for 30 minutes and at room temperature for 1 hour. After the reaction, the reaction liquid was added to 200 ml of n-hexane, and the product cyclopentadienyl lithium was precipitated, collected by filtration by means of a glass filter and dried.

Preparation of Organic Silane Compound Having Such a Structure that a Secondary Carbon Atom is Directly Bonded to a Silicon Atom 50 ml of dry n-pentane, 20 ml of dry ether and 8.09 g (47.6 mmol) of tetrachlorosilane were charged in a 200 ml Schlenk tube reactor equipped with a stirring apparatus in a stream of nitrogen, and a liquid having 7.20 g (100 mmol) of the above prepared cyclopentadienyl lithium slurried with 70 ml of n-pentane was dropwise added thereto by means of an injector at room temperature over a period of 10 minutes. After completion of the dropwise addition, stirring was carried out at room temperature for 24 hours. After completion of the reaction, lithium chloride was removed from the reaction liquid slurry by means of a glass filter, and n-pentane was distilled off to obtain dicyclopentadienyldichlorosilane.

The obtained dicyclopentadienyldichlorosilane and 120 ml of n-hexane were charged in a 200 ml Schlenk tube reactor equipped with a reflux condenser and a stirring apparatus in a stream of nitrogen and dissolved. 8.17 g (120 mmol) of sodium ethoxide was added thereto, and reaction was carried out under reflux of n-hexane for 4 hours. After the reaction, sodium chloride and unreacted sodium ethoxide were removed by filtration by means of a glass filter, and 7.41 g (29.9 mmol) of the product dicyclopentadienyldiethoxysilane was obtained by purification by distillation. The percentage of yield was 62.8%.

The results of analysis of the isolated dicyclopentadienyldiethoxysilane by $^1$H-NMR and GC-MS were as follows.

$^1$H-NMR: 6.25 ppm (m, 10H), 1.28 ppm (t, 6H), 3.91 ppm (q, 4H)

GC-MS: Mw=248, $C_{14}H_{20}O_2Si$

Further, the water content and the sodium and lithium contents in 100 g of the obtained dicyclopentadienyldiethoxysilane were measured by means of a Karl Fischer moisture meter and ICP-MS (inductively coupled plasma mass spectrometer, manufactured by Yokogawa Analytical Systems, Inc., tradename "HP4500") and as a result, $H_2O$=17 ppm, Li<10 ppb and Na<10 ppb, and the obtained product was useful as an insulating film material.

Comparative Example 6

The same operation as in Example 1 was carried out except that after the reaction of dicyclopentadienyldichlorosilane with sodium ethoxide in "Preparation of organic silane compound having such a structure that a secondary carbon atom is directly bonded to a silicon atom" in Example 10, sodium chloride and unreacted sodium ethoxide were not removed by filtration, but water was added to carry out removal of the solution by separation and extraction to prepare dicyclopentadienyldiethoxysilane.

The water content and the sodium and lithium contents in the obtained dicyclopentadienyldiethoxysilane were measured by means of a Karl Fischer moisture meter and ICP-MS and as a result, $H_2O$=130 ppm, Li<10 ppb and Na<10 ppb, and the obtained product was inappropriate as an insulating film material.

According to the present invention, the following remarkable effects are obtained.

The present invention provides a material having a low dielectric constant and a high mechanical strength, as a low-dielectric constant material for an interlayer insulating film of a semiconductor device, by using the organic silane compound having such a structure that at least one secondary hydrocarbon group and/or tertiary hydrocarbon group is directly bonded to a silicon atom of the present invention.

The present invention further provides a porous material which can hardly be obtained by a Conventional method, by applying the organic silane compound having such a structure that at least one secondary hydrocarbon group and/or tertiary hydrocarbon group is directly bonded to a silicon atom to formation of an interlayer insulating film by PECVD.

The entire disclosures of Japanese Patent Application No. 2002-023988 filed on Jan. 31, 2002, Japanese Patent Application No. 2002-112130 filed on Apr. 15, 2002, Japanese Patent Application No. 2002-332100 filed on Nov. 15, 2002, Japanese Patent Application No. 2002-346225 filed on Nov. 28, 2002 and Japanese Patent Application No. 2002-346226 filed on Nov. 28, 2002 including specifications, claims, drawings and summaries are incorporated herein by reference in their entireties.

What is claimed is:

1. A film formed by the process which comprises forming the film by chemical vapor deposition from a precursor material, which precursor material contains an organic silane compound having such a structure that at least one secondary hydrocarbon group and/or tertiary hydrocarbon group is directly bonded to a silicon atom and which is represented by formula (2):

wherein the organic silane compound has such a structure that a tertiary hydrocarbon group is directly bonded to a silicon atom and has the following formula (2):

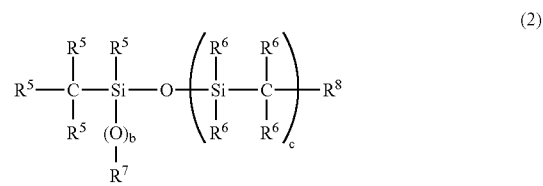

wherein each of $R^5$ and $R^6$ is a $C_{1-20}$ hydrocarbon group, each of $R^7$ and $R^8$ is a hydrogen atom or a $C_{1-20}$ hydrocarbon group, provided that a plurality of $R^5$'s, or $R^6$ and $R^8$ may be bonded to each other to form a cyclic structure, and each of b and c is 0.

2. The film of claim 1 which is an insulating film.

3. The film of claim 2 which is obtained by subjecting the insulating film as defined in claim 2 to a heat treatment at a temperature at which the bond between the tertiary carbon atom and the silicon atom is broken or higher, to make the film porous.

4. A semiconductor device, which employs the insulating film as defined in claim 2.

* * * * *